(12) United States Patent
Han et al.

(10) Patent No.: US 6,470,749 B1
(45) Date of Patent: Oct. 29, 2002

(54) METHOD AND APPARATUS FOR PULSED ULTRASONIC DOPPLER MEASUREMENT OF WALL DEPOSITION

(75) Inventors: Wei Han, Missouri City; James R. Birchak, Spring; Crispin L. Richards, Houston; Vimal V. Shah, Houston; Bruce H. Storm, Houston; Rajnikant M. Amin, Houston, all of TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 09/851,509

(22) Filed: May 8, 2001

(51) Int. Cl.$^7$ .............................................. G01N 29/00
(52) U.S. Cl. ........................................ 73/622; 73/609
(58) Field of Search .................. 73/609, 610, 618, 73/620, 622, 624, 625, 627, 628, 629, 596, 597; 600/454, 455

(56) References Cited

U.S. PATENT DOCUMENTS

| | | | |
|---|---|---|---|
| 4,437,332 A | 3/1984 | Pittaro | 73/1 |
| 4,545,248 A | 10/1985 | Kitada et al. | 73/597 |
| 4,770,184 A * | 9/1988 | Greene, Jr. et al. | 600/454 |
| 5,092,176 A | 3/1992 | Buttram et al. | 73/599 |
| 5,327,893 A | 7/1994 | Savic | 128/661.08 |
| 5,555,886 A * | 9/1996 | Weng et al. | 600/454 |
| 5,657,760 A | 8/1997 | Ying et al. | 128/660.03 |
| 5,756,898 A * | 5/1998 | Diatschenko et al. | 73/592 |

* cited by examiner

Primary Examiner—Richard A. Moller
(74) Attorney, Agent, or Firm—Conley, Rose & Tayon P. C.

(57) ABSTRACT

A method for monitoring and measuring the buildup of deposits on the inner surface of a pipeline containing flowing fluid comprises (a) transmitting a first acoustic signal into the pipeline through the pipeline wall, (b) receiving echoes of the transmitted signal, and (c) determining from the received echoes how far from the pipeline inner surface the interface between the deposits and the flowing fluid lies. An alternative method for monitoring and measuring the buildup of deposits on the inner surface of a pipeline containing flowing fluid comprises (a) transmitting a first acoustic signal into the pipeline through the pipeline wall, (b) receiving echoes of the signal, and (c) using the Doppler frequency shift of the received echoes to determine how far from the pipeline inner surface the interface between the deposits and the flowing fluid lies. An apparatus for monitoring and measuring the buildup of deposits on the inner surface of a pipeline containing flowing fluid, comprises a first transmitter in acoustic communication with the pipeline wall and generating a transmitted signal, a first receiver in acoustic communication with the pipeline wall generating received echo signal from a received signal comprising the reflection of the transmitted signal off the flowing fluid, and a microprocessor for determining from the received echo signal how far from the pipeline inner surface the interface between the deposits and the flowing fluid lies.

21 Claims, 5 Drawing Sheets

METHOD AND APPARATUS FOR PULSED ULTRASONIC DOPPLER MEASUREMENT OF WALL DEPOSITION

CROSS-REFERENCE TO RELATED APPLICATIONS

Not applicable.

STATEMENT REGARDING FEDERALLY SPONSORED RESEARCH OR DEVELOPMENT

Not Applicable.

TECHNIAL FIELD OF THE INVENTION

The present invention relates generally to a method and apparatus for measuring the thickness of a layer of solids deposited on an inner pipeline surface. The thickness is determined from the Doppler frequency shift resulting from the local flow velocity at pre-determined distances away from the inner pipe wall. The present method and apparatus provide non-invasive, qualitative detection of solids buildup and quantitative measurement of thickness of solids on an inner pipe wall.

BACKGROUND OF THE INVENTION

As the current trend in offshore oil and gas production advances into deeper waters, it is becoming increasingly necessary for the industry to develop cost-effective solutions for developing fields in deep and/or remote waters.

A typical solution for such cases is to keep the production facilities on a "host platform" and connect the deep-water well(s) to the platform with pipelines and risers. The supporting equipment for the subsea tree control, such as hydraulic and electric power units, chemical injection pumps and tanks, and a control console, are also housed on the host platform. The subsea tree control is accomplished via long umbilical(s) consisting of electric conductors, hydraulic lines and chemical injection lines laid alongside the pipeline. In addition, two parallel pipelines are necessary to accomplish the roundtrip pigging operations. The distance between the well and the host platform is known as the tieback distance. The cost and technical challenges of this type of conventional tieback system increase as the tieback distance increases, and to a lesser extent as the water depth increases. In most cases, 20 miles represents the practical limit for the maximum tieback distance with the conventional tieback system.

One limit on the length of subsea tiebacks conveying crude petroleum arises from flow assurance problems. Solids such as asphaltene and paraffin deposit on the inner walls of the tiebacks and partially, and in some cases completely, block the flow. The longer the tieback is, the greater the length of pipe that must be inspected and kept free of deposits.

At present, non-intrusive sensors that can adequately detect and characterize such deposits are not available. The present solutions require use of very expensive alternative methods for flow assurance, including twin flowlines (for round-trip pigging), heat traced or insulated tiebacks and pipelines. These alternative methods operate by attempting to prevent the deposition of solids on the flowline wall, and do not provide means for detecting the presence of solids in the event that deposits occur. The lack of continuous monitoring can result in undesirable shutdowns. For example, if a flowline has been kept clear by pigging at a certain frequency, e.g. once per month, and the composition of the fluid in the flowline changes so that deposits begin to form at a greater rate, the line will become clogged and possibly shut down because the previously established pigging frequency is now insufficient.

Some attempts have been made to provide systems for monitoring solids buildup. For example, monitoring devices such as that described in U.S. Pat. No. 4,490,679 identify paraffin by monitoring change in the resistance of an electromagnetic coil. The monitoring device requires access to the fluid and is housed in a recess in the pipe. It is desired to provide monitoring without disrupting the flow of fluid through the line and without requiring direct contact with the fluid.

Similarly, the optical asphaltene sensor described in U.S. Pat. No. 4,843,247 determines the content of asphaltene in heavy oils based on the absorption spectra of asphaltene. The invention uses visible light having wavelengths in the range of 500 nm to 1000 nm and thus requires at least optical transmission through the fluid, which is difficult to operate in a pipeline and prone to the coating of hydrocarbons on the optical windows that may distort the results.

There are other industrial applications in which it is desirable to measure thickness of a particular layer or object. For example, U.S. Pat. No. 5,929,349 discloses an ultrasonic inspecting tool that can be used to measure the thickness of a tank wall. U.S. Patent No. 5,092,176 provides a method for determining deposit buildup on the inner surface of a boiler tube by measuring sound attenuation in multiple echoes from the wall-deposit interface. To give an accurate measurement, the boiler tube must be empty of water so as to enhance the acoustic reflection by increasing the acoustic impedance mismatch between the deposit —air interface. If the tube is not emptied of fluid, the acoustic signals will be largely transmitted into the fluid in the tube and prevent accurate measurements. U.S. Pat. No. 5,734,098 provides a method for measuring mass deposition on the surface of a thickness-shear mode quartz resonator based on the resonance response of the piezoelectric crystal that is immersed in a fluid.

Conventional ultrasonic devices for measuring thickness are not always reliable for determining the thickness of a layer of deposited solids, however, because the acoustic impedance of the deposited material may be close to or even match the impedance of the adjacent liquid, with the result that little or no reflection is obtained from the surface of the deposited layer.

Hence, it is desired to provide a system that can operate over greater tieback distances without the cost and technical disadvantages that heretofore have prevented increasing the tieback distance. It is specifically desired to provide a method and apparatus for detecting deposits of asphaltene and paraffin on the inside wall of a pipeline without interrupting the flow of fluid through the pipeline. It is further desired to provide a robust system can measure the thickness of the deposited layer even if the acoustic impedance of the deposited layer and the Showing liquid match.

Another technique for measuring solids in a fluid passageway involves the use of Doppler backscattering. For example, Doppler backscattering techniques are used to monitoring tissue damage and to detect deposits in arteries. U.S. Pat. No. 5,657,760 to Ying et al. discloses a method of monitoring the extent and geometry of tissue that has undergone thermal treatment. The apparatus measures the phase change and amplitude of received echoes at multiple range depths to monitor the tissue thermal profile and geometry of tissue thermal damage. U.S. Pat. No. 5,327,893 to Savic discloses a method for detection of cholesterol deposits in arteries based on received acoustic signals with Doppler frequency shifts as result of artery heartbeat movement. The signals are analyzed by a pattern recognition technique that allows recognition of the artery with stenosis. U.S. Pat. No. 4,770,184 to Greene et al. provides a diagnostic system for monitoring human arteries based on comparison of the time-and frequency-domain Doppler signals of patients to those of normal people. These in vivo applications are different from the subsea invention in which it is currently desired to provide quantitative deposition measurement, based on measuring the Doppler frequency shifts resulting from the movement of the particulate in a fluid stream, and based on the known pipe wall thickness.

Hence, there is still a need for a reliable acoustic means for detecting and measuring wall deposition in subsea pipelines. In particular, the desired system should be robust enough to function in a subsea environment. The desired system should also be able to provide the desired measurements even when the acoustic impedance of the deposition layer and the flowing liquid match are the same or similar.

SUMMARY OF THE INVENTION

The present invention comprises a system including a method and apparatus for measuring the thickness of a layer of solids deposited on an inner pipeline surface. More specifically, the present system provides a method and apparatus for detecting deposits of asphaltene and paraffin on the inside wall of a pipeline. The present system can operate over extended tieback distances without incurring prohibitive costs and technical disadvantages. The present system is robust and can measure the thickness of the deposited layer even if the toustic impedance of the deposited layer and the flowing liquid match.

According to a preferred embodiment, the thickness of a deposited solid or semi-solid layer is determined from the Doppler frequency shift that results from the local flow velocity at a plurality of pre-determined distances from the inner pipe wall. The presence of deposited solids is detected by comparing the timing of the reflection of the inner surface of the pipe wall with the extra propagation time for the signal to reach flowing fluid. The thickness of the deposited layer is determined from the position of the innermost zero Doppler frequency shift, which may be extrapolated from the close-wall Doppler frequency shifts, and from the position of the inner pipe wall surface. The disclosed method and apparatus provide non-invasive, qualitative detection of deposition buildup and quantitative measurement of deposited solids on an inner pipe wall. Another embodiment of the invention comprises a method for monitoring and measuring the buildup of deposits on the inner surface of a pipeline containing flowing fluid, comprising: (a) transmitting a first acoustic signal into the pipeline through the pipeline wall, (b) receiving echoes of the transmitted signal, and (c) determining from the received echoes how far from the pipeline inner surface the interface between the deposits and the flowing fluid lies. Step (c) can include using the Doppler frequency shift of echoes from the flowing fluid to locate the deposit-fluid interface, and/or measuring the Doppler frequency shift of the echoes from at least two points in the flowing fluid and extrapolating the location of the zero velocity. The echo analysis can include time-gating the echoes. The transmitted signal need not be normal to the pipeline axis. In addition, more than one transmitter and/or more than one receiver can be used in the present method.

In still another embodiment, the present apparatus for monitoringand measuring the buildup of deposits on the inner surface of a pipeline containing flowing fluid, comprises: a first transmitter in acoustic communication with the pipeline wall and generating a transmitted signal, a first receiver in acoustic communication with the pipeline wall and generating received echo signal from a received signal comprising the reflection of the transmitted signal off the flowing fluid, and a microprocessor for determining from the received echo signal how far from the pipeline inner surface the interface between the deposits and the flowing fluid lies.

BRIEF DESCRIPTION OF THE DRAWINGS

For a more detailed understanding of the present invention, reference will be made to the accompanying Figures, wherein:

FIGS. 3(A–E) are schematic illustrations of, respectively: transducers and material media (A), transmission signal (B), received echoes (C), signal range gating (D), and Doppler frequencies for the gated echoes (E);

DETAILED DESCRIPTION OF THE PREFERRED EMBODIMENTS

Figure 1:
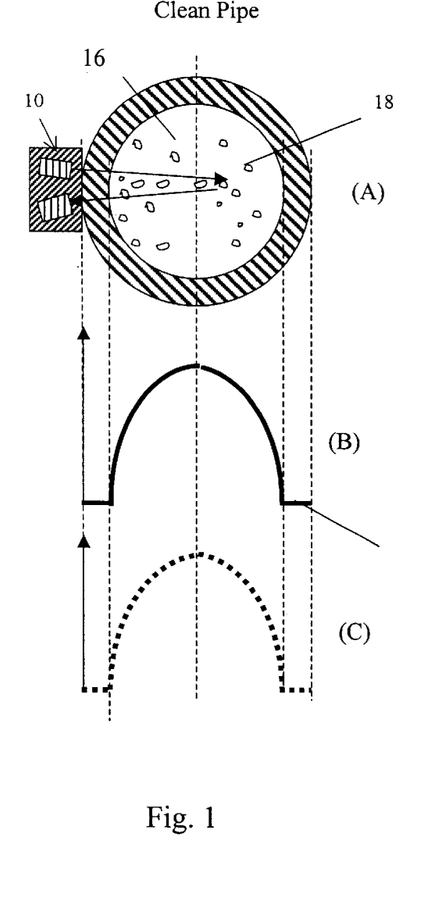
FIGS. 1(A)–1(C) are schematic illustrations of, respectively: a pipe including a sensor according to the present invention, a plot of the fluid flow velocity in the pipe of FIG. 1(A), and a plot of the Doppler backscattering of resulting from the velocity pattern shown in FIG. 1(B), respectively, wherein the inside of the pipe wall is free of deposited material.
Figure 2:
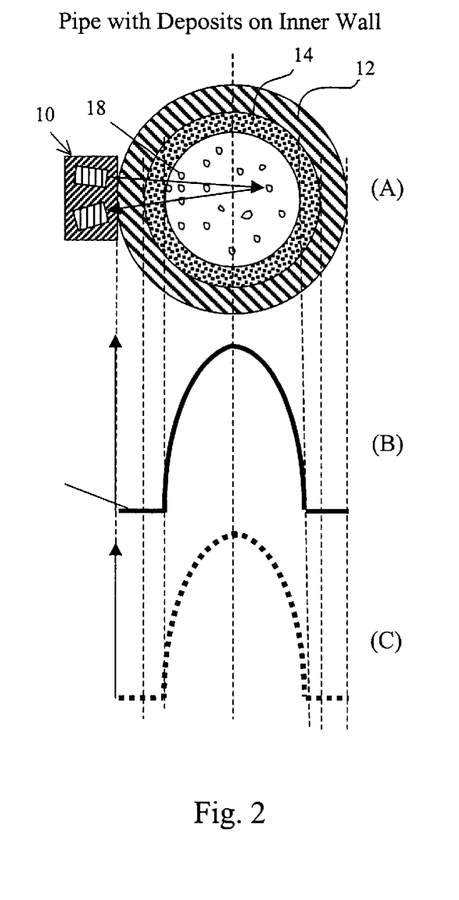
FIGS. 2(A)–2(C) are schematic illustrations of, respectively: a pipe including a sensor according to the present invention, a plot of the fluid flow velocity in the pipe of FIG. 2(A), and a plot of the Doppler backscattering of resulting from the velocity pattern shown in FIG. 2(B), wherein a layer of deposited material is present on the inside of the pipe wall.

The present method for measuring the thickness of deposited layers is based on detection of a Doppler signal (Doppler frequency shift) caused by fluid flowing in the pipeline. FIGS. 1 and 2 are schematic cross-sectional illustrations of a Doppler sensor 10 mounted on a pipe wall 12. A fluid 16 flows through the pipe. In FIG. 1, the pipe wall 12 is free of deposits and in FIG. 2 a layer 14 of deposited solids or semi-solids is present on pipe wall 12.

According to a preferred embodiment, the thickness of deposited layer 14 is measured by detecting a Doppler frequency shift due to the change in fluid flow velocity as a function of distance from pipe wall 12. Fluid 16 inside the pipeline normally contains acoustic scatterers 18, such as solid particles, droplets of immiscible fluid, gas bubbles, or vortex rurbulence. Because the scatterers are moving with respect to the pipe wall, an ultrasonic tone-burst pulse wave 20 transmitted into flowing fluid 16 through pipe wall 12 wave will be reflected by those scatterers with a frequency shift. The shift in frequency that results when a wave is reflected by an object moving with a velocity component in the direction of the wave is called the Doppler frequency shift. The Doppler frequency shift is linearly proportional to the flow velocity of the scatterers.

While a wave reflected by an object moving with a velocity component in the direction of the wave will undergo a frequency shift, a wave reflected by an object that is not moving will not. Hence, a wave transmitted into the pipe and reflected by either the pipe wall-deposit interface or the deposit-fluid interface will not be frequency shifted, as neither interface is moving.

By way of illustration, FIGS. 1(B) and 2(B) show the radial velocity profiles for fluid 16 flowing through pipes of FIGS. 1(A) and 2(A), respectively, and FIGS. 1(C) and 2(C) show the Doppler signals corresponding to the velocity profiles of FIGS. 1(B) and 2(B). For the clean pipe shown in FIG. 1, the Doppler signal starts at the inner surface of the pipe wall (the pipe wall-deposit interface), while in a pipe containing deposits as shown in FIG. 2, the Doppler signal starts at the deposit-fluid interface.

Figure 3:
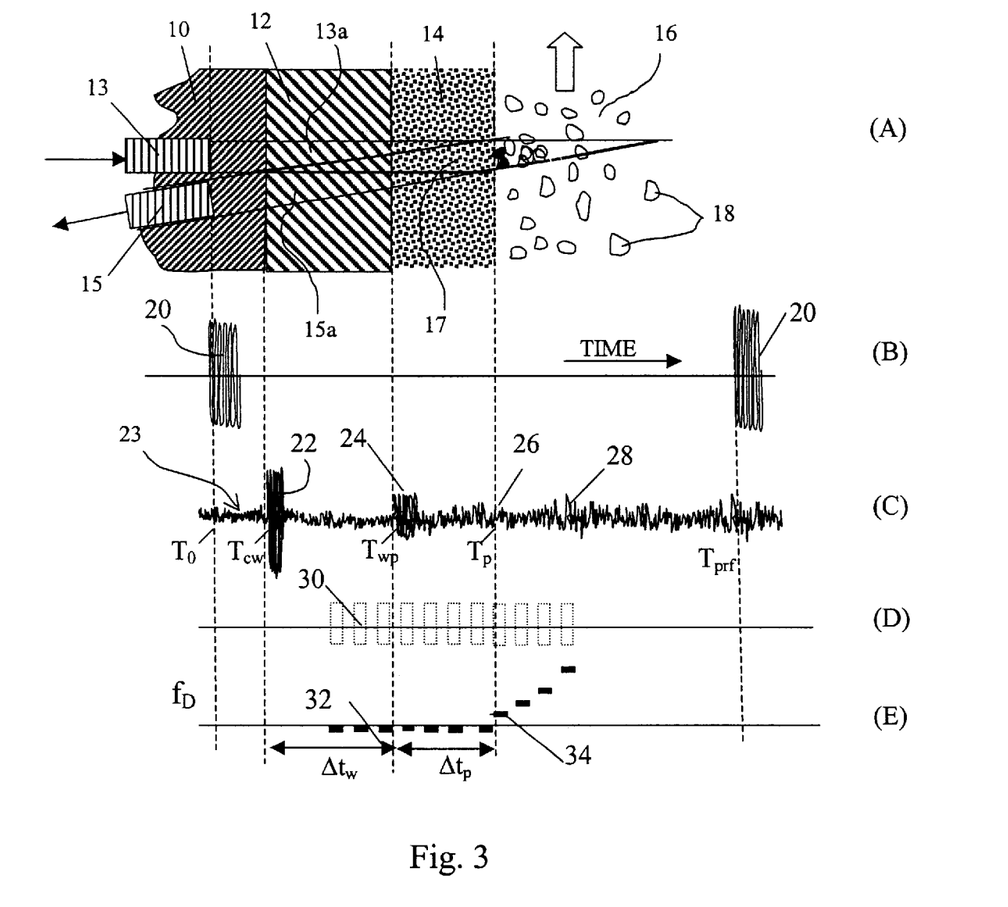

Referring now to FIG. 3(A), in one preferred embodiment, the present acoustic transducers include a piezoelectric transmitter 13 and a receiver 15, mounted outside of the pipe wall 12. Adjacent to pipe wall 12 is deposit layer 14, and adjacent to deposit layer 14 is flowing fluid 16. A coupling medium acoustically couples the transducers to the pipe wall 12. The coupling medium is preferably effective for transmitting the signal between the transducers and the pipe wall with a minimal amount of loss. To ensure the detection of reflected echoes from various interfaces and scattering particles, the transmitter and receiver each preferably comprise a focused transducer.

Since it is preferred to use focused transducers, the "beams" or active regions 13a, 15a for transducers 13 and 15 respectively are shown. It is preferred that the region where beams 13a and 15a intersect, hereinafter referred to as the "insonificaton volume" 17, include the water-pipe wall interface, the pipe wall-deposit interface, and the deposit-fluid interface. It is particularly preferred that insonification volume 17 include a portion of flowing fluid 16 and riculates 18. It is further preferred, but not necessary, that the insonificaton volume include the pipe axis. The extent of the insonificaton volume can be adjusted by adjusting distance and angle at which the transmitter and receiver are mounted. In an alternative embodiment, one or both of the transducers can be also mounted inside the pipe wall to further enhance the transmission of sound energy into the fluid flow.

In one embodiment, the angle of the transmitting transducer 13 is preferably normal to the flow direction ($\theta_{T=90}°$) to maximize signal transmission, while receiving transducer 15 is positioned at an oblique angle $\theta_R$ to the flow direction to detect echoes from various interfaces. Alternatively, depending in part on the nature of the fluid in the pipe and the degree of solids buildup, angling one or both transducers 13, 15 with respect to the flow direction may allow better detection of flow velocity, since flow that is precisely normal to the signal direction will appear to have a velocity of zero when measured using Doppler frequency shifting. Hence, in another embodiment, transducers 13, 15 are positioned diametrically across from each other on pipe wall 12 and are both angled with respect to flow such that signals from transmitter 13 are reflected and received from a particle that is some axial distance upstream or downstream in the pipe. If the insonification volume 17 is upstream of the transducers, the frequency of the signal will be shifted in one direction (increased), whereas if the insonification volume 17 is downstream of the transducers, the frequency of the signal will be shifted in the opposite direction (decreased), Referring briefly to FIGS. 3(B)–(E), the various signals are shown according to their time and range relationships. FIG. 3(B) shows a burst of sine waves 20, which excites the transmitter 13 at time $T_0$ with a repetitive time interval $T_{prf}=1/f_{prf}$. FIG. 3(C) shows a train of echo signal 23 received at receiver 15. Echo signal 23 indicates the coupling medium-pipe wall interface 22 at time $T_{cw}$, the pipe wall-deposit interface 24 at time $T_{wp}$, and backscattered signals 28 from the fluid, yet does not reveal any Doppler shift. While the wall-deposit interface echo 24 may sometime be too weak to be noted, nevertheless its arrival timing $T_{wp}$ can be estimated based on the known wall thickness and speed of sound of the pipe FIG. 3(D) illustrates the sampling gates that define finite portions of the received echo 23 to be sampled for separate processing.

Because the velocities of the acoustic signal in the coupling medium and the pipe wall material are known, the distance that the signal travels in each medium corresponds to a particular time delay. With the known distance between the transducer and the pipe wall, the time for the reflected echo 24 from the water-pipe wall interface $T_{cw}$ can be calculated. Because thickness of the pipe wall is known, the time interval for the pulse reflection signal inside the pipe wall is given by $\Delta T_w = 2 W^*(1/\sin \theta_R)/ C_w$, where, W is the pipe wall thickness and $C_w$ is the longitudinal speed of sound in the pipe wall material. $\Delta T_w$ determines the delay time of the pulse having one round-trip within the pipe wall. Therefore, the delay time for the received echo 26 from the pipe wall-deposit interface is determined by $T_{wp}=\Delta T_w+T_{cw}$, where $T_{cw}$ and $\Delta T_w$ have been determined as above. As the acoustic signal propagates further into the deposition layer and into the flowing fluid stream, echoes consisting of reflected signals 26 from the deposit-fluid interface and backscattered signals 28 from the particulate in the fluid are received. Very often, like the wall-deposit interface echo 24, the received echo 26 from deposit-fluid interface may be very weak.

Figure 4:
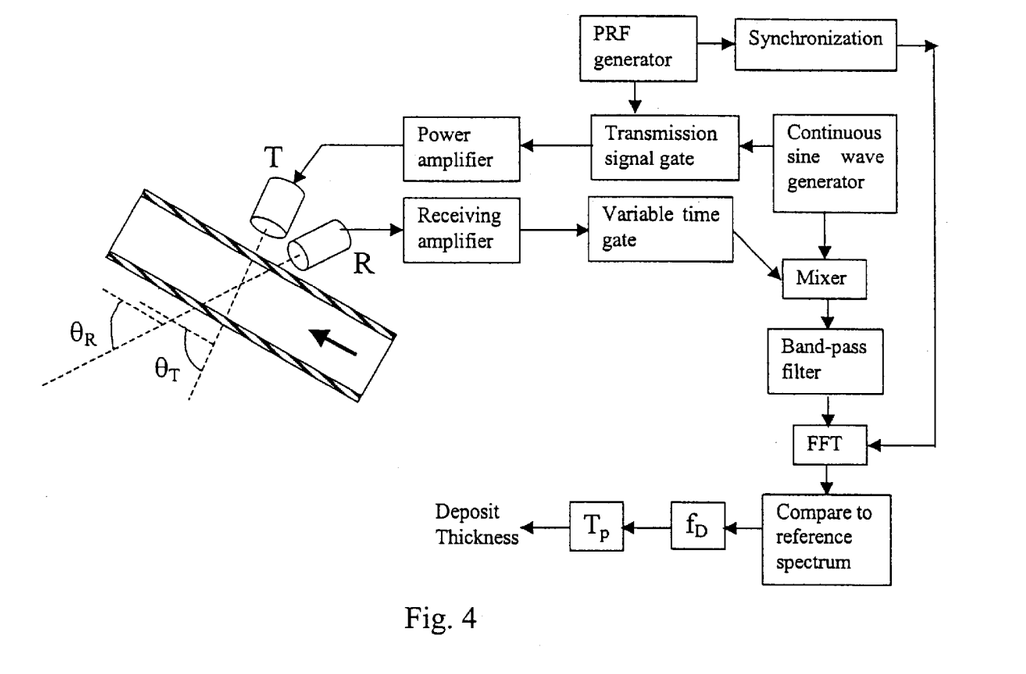
FIG. 4 is a schematic illustration of the pulsed Doppler measurement principles of the present invention.

According to one preferred embodiment as shown in FIG. 4, acoustic signal 20 is generated in the following manner. A sinusoid wave function generator emits a reference frequency of a few megahertz. The reference sine wave is fed into a gating module that allows transmission of just a few cycles of the reference signal at a predetermined time interval. The gating module is controlled by a pulse repetitive frequency (PRF) generator. This system produces a train of ultrasonic bursts of the reference frequency. The bursts may typically have a repetition frequency $f_{prf}$ of about $f_{prf}=10$ kHz. The pulse train is the input to a power amplifier and then fed into the transmitting transducer. As the acoustic bust propagates through the pipe wall and fluid and then bounces back, a continuous train of echoes is amplified by a pre-amplifier and detected by the receiving transducer. The received signals are then fed into a time range gate, which opens at the PRF rate and collects signals of a pre-determined length at a pre-determined time delay.

By altering the delay time of the time gate, Doppler frequency shift (velocity) and range information about the deposited layer can be obtained. After a given time delay from the beginning of pulse transmission and reflection in the pipe wall, $T_0+\Delta t_w$, the gate opens and samples the received echoes, as shown in FIG. 3(D). The gated echoes are then mixed with the reference frequency wave of the transmission bursts, to detect the change in phase. The phase variations over many pulse repetition cycles for this gated signal reveal a modulated waveform that contains high frequency components as result of the carrier frequency (in megahertz range), the pulse repetitive frequency (e.g., about 10 kHz), and lower frequency components of Doppler frequency shift (up to a few kHz). The output signals are fed into a band-passfilter. Frequency components above one half of the pulse repetitive frequency are removed. Similarly, frequency components below 50–100 Hz are associated primarily with slow movement of the deposit-fluid interface, and are thus also filtered out. The resulting demodulated signal produces a Doppler frequency spectrum with mean frequency $f_D$ corresponding to the averaged flow velocity of the patculate from within the gated sample cell. (By varying the delay time of the gate and processing the Doppler spectrum for each of the sampling cell, a profile of mean Doppler frequency over the delay time can be obtained, as shown in FIG. 3(E).

The net output signal thus contains only the Doppler shift frequency associated with the flow velocity. This is fed into a Fast Fourier Transform analyzer to reveal its frequency shift spectrum. Therefore, the flow of the fluid in the sampled volume that can be detected and the mean flow velocity V can be determined from the frequency spectrum according to Equation (1).

$$V = f_D * c / [f_0 * (\cos \Delta_T + \cos \Delta_R)] \quad (1)$$

where $f_D$ is the mean Doppler frequency shift of the spectrum, $f_0$ is the transmitting frequency, c is the speed of sound in the fluid, and $\Delta_T$ and $\Delta_R$ are the angles of the transmitter and receiver with respect to the direction of the flow, respectively.

By scanning a range of time gates across the pipe cross section and measuring the Doppler frequency in each gated sample, qualitative indication of the fluid flow profile can be obtained. If the time gate is set within the deposited material, the amplitude of Doppler spectrum will be close to zero, since there is no fluid flow in this sampled volume. If the time gate is set on a volume in the moving fluid stream, a Doppler frequency shift will occur.

The mean frequencies $f_D$ for the time gates in FIG. 3(D) are plotted in FIG. 3(E). Plotting the mean Doppler frequency for each gated echo as function of time reveals the edge 34 of the fluid flow, which occurs at time $T_p$, where the Doppler spectrum amplitudes begin to exceed a predetermined threshold amplitude. The time-of-flight in the deposit $\Delta t_p$ is determined according to Equation (2).

$$\Delta t_p = T_p - T_{cw} - \Delta t_w = T_p - T_{wp} \quad (2)$$

Figure 5:
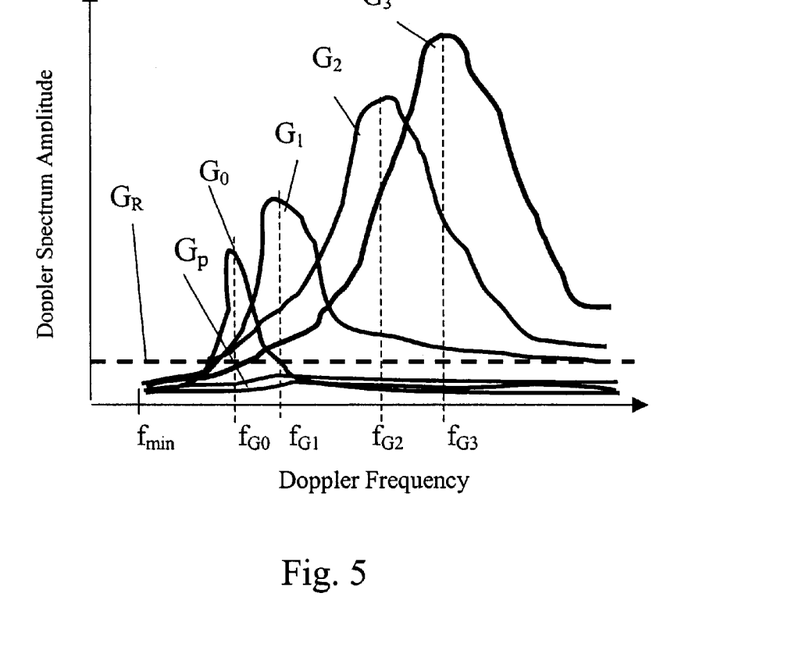
FIG. 5 is an exemplary plot showing the various Doppler frequency spectra obtained from gated echoes from varying radiuses within a pipe.
Figure 6:
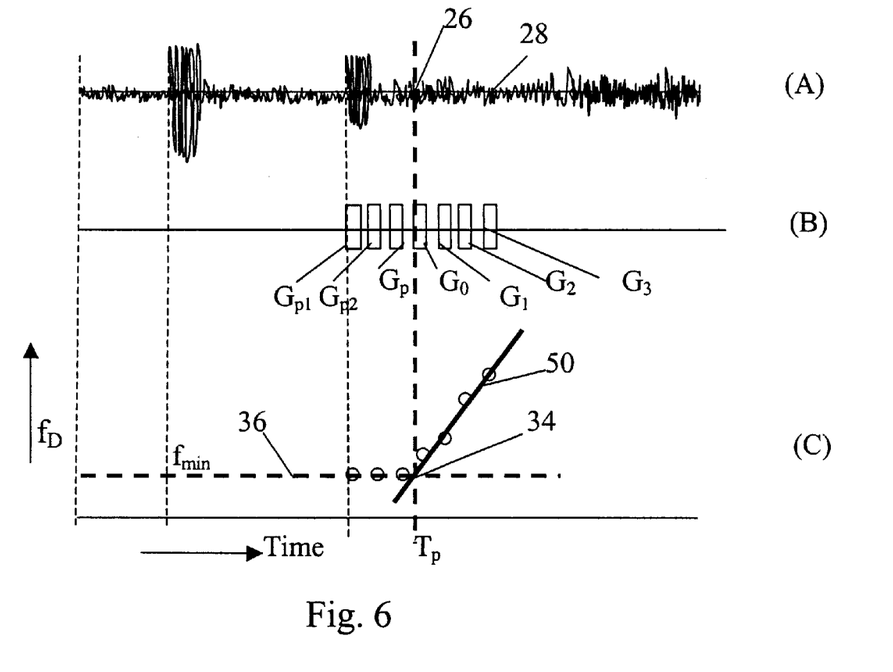
FIGS. 6(A)–6(C) are schematic illustrations of the signal of FIG. 5 showing, respectively, the received echo train (A), a range of time gates (B), and the mean Doppler frequencies from those gated echoes (C)

To determine the thickness of deposition layer, the time to the start of flow in the train of received echoes (or range position), $T_p$, has to be measured accurately. The start time is determined by moving the sampling gate and comparing the resulting Doppler frequency shift spectra to a reference threshold frequency shift spectrum. A spectrum obtained from the signal gate that is inside the pipe wall may be used as the reference spectrum. As the gate is shifted radially inward through pipe wall 12 and deposit layer 14, the Doppler spectrum amplitude is close to the reference spectrum in the region where no flow occurs. The reference spectrum is normally caused by instrumental background electronic noise and/or vibrational noise of the pipe wall. Observation of a Doppler spectrum having an amplitude greater than that of the reference indicates fluid flow. Hence, $T_p$ is determined from that particular time range, as shown in FIG. 3(D). In an alternative embodiment, the starting range (or time) for echoes received from the fluid, is extrapolated using the measured mean frequencies from the Doppler frequency spectra for a range of time gates, as shown in FIGS. 5 and 6 and discussed. in detail below.

Using $T_p$, the thickness of the deposited layer can be calculated as $D_p = (T_p - T_{wp}) * c_p / 2 = \Delta t_p * c_p / 2$, where $T_{wp}$ is the time of reflected echo from the pipe wall/deposit interface and $c_p$ is the speed of sound in the deposition material.

Measurement of $T_p$ can be used to detect and monitor the deposition buildup on the pipe wall. Normally, the pipe wall thickness is known, so $T_{wp}$ is constant. For clean pipe wall with no deposit buildup, the Doppler frequency shift will indicate that flow begins at the inner surface of the pipe wall, i.e., $T_p = T_{wp}$. Otherwise, deposit on the wall is detected if $T_p > T_{wp}$, since the flow begins at a point radially inward from the inner wall.

The resolution and accuracy of the thickness of deposited layers measurement using the above Doppler frequency shift approach. depends on several important factors, including time gate width, gate incremental interval, minimum detectable Doppler frequency shift, Doppler frequency shift resolution, and wavelength of the ultrasound pulse. Use of shorter time gate widths increases the deposition thickness resolution. The minimum detectable Doppler frequency is the lower frequency limit set by the band-pass filter, which is normally about 50–100 Hz. For $f_D = 100$ Hz, the minimum velocity in the fluid is about V=0.062 m/s according to Eq. (1), if c=1300 m/s, $\theta_T = 90°$, $\theta_R = 20°$, and $f_0 = 7.0$ MHz. The FFT analyzer for Doppler frequency shift measurement typically has a resolution of 10 Hz, corresponding to about 0.0062 m/s velocity resolution according to the above parameters used. The resolution of the present method can be increased by shortening time gate widths and shortening incremental interval, but longer time for the signal sampling and processing will be required, due to the increased data collection rate. Likewise, increasing transmitting frequency may result in higher range resolution, but at the expense of higher attenuation of sound waves in various material media.

FIG. 4 gives a schematic illustration of one preferred system and a preferred series of steps that can be performed to achieve measurements in accordance with the present invention. It will be understood that different apparatus can be used. Similarly that the steps can be performed in a different order, and/or additional steps, such as signal averaging, noise filtering and the like can be added without departing from the scope of the present invention.

Referring briefly to FIG. 5, an exemplary plot shows the various Doppler frequency spectra obtained from gated echoes from varying positions within the pipe. In FIG. 5, $f_{min}$ is the minimum frequency, for example, of 100 Hz set by the lower limit of band-pass filter. $G_R$ is the threshold amplitude level of a reference Doppler spectrum. $G_{p1}$, $G_{p2}$, and $G_{p3}$, with amplitudes lower than the threshold amplitude $G_R$, are the frequency spectra obtained for samples positioned inside the deposition layer. $G_0$, $G_1$, $G_2$, and $G_3$ are Doppler spectra obtained for gates positioned inside the flow stream, where $G_0$ is the beginning of the gate inside the deposited layer. $f_{G0}$, $f_{G1}$, $f_{G2}$, $f_{G3}$ are the corresponding mean frequencies for these gated echoes. FIG. 5 illustrates how the start time of the flow in the echo train, $T_p$, can be accurately determined by extrapolating the measured mean Doppler frequencies from the various gated samples inside the flow stream as indicated by reference numeral 50 to zero frequency as indicated by reference numeral 36. Using this technique, the thickness of the deposited layer can be calculated according to $D_p=(T_p-)*cp/2$, $T_{wp})*C_p/2$, where $T_{wp}$ is the time of reflected echo from the pipe wall/deposit interface and $C_p$ is the longitudinal speed of sound in the deposition material. FIG. 6 shows a schematic illustration of the received echo train (A), a range of time gates (B), and the mean Doppler frequencies from those gated echoes. The start position of the flow, $T_p$ in time (34), can be determined by extrapolating from the mean frequencies (50).

Figure 7:
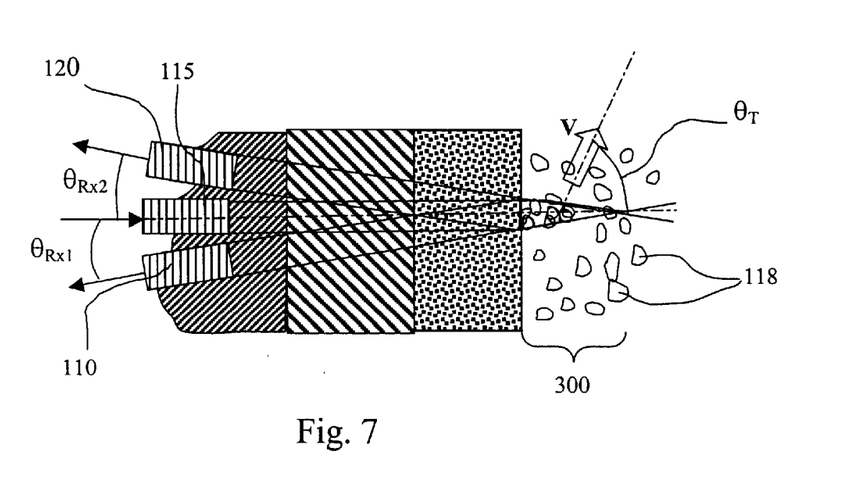
FIG. 7 is a schematic illustration of an alternative embodiment in which a plurality of relatively angled transducers are used to detect the direction of flow of reflectors in fluid.
Figure 8:
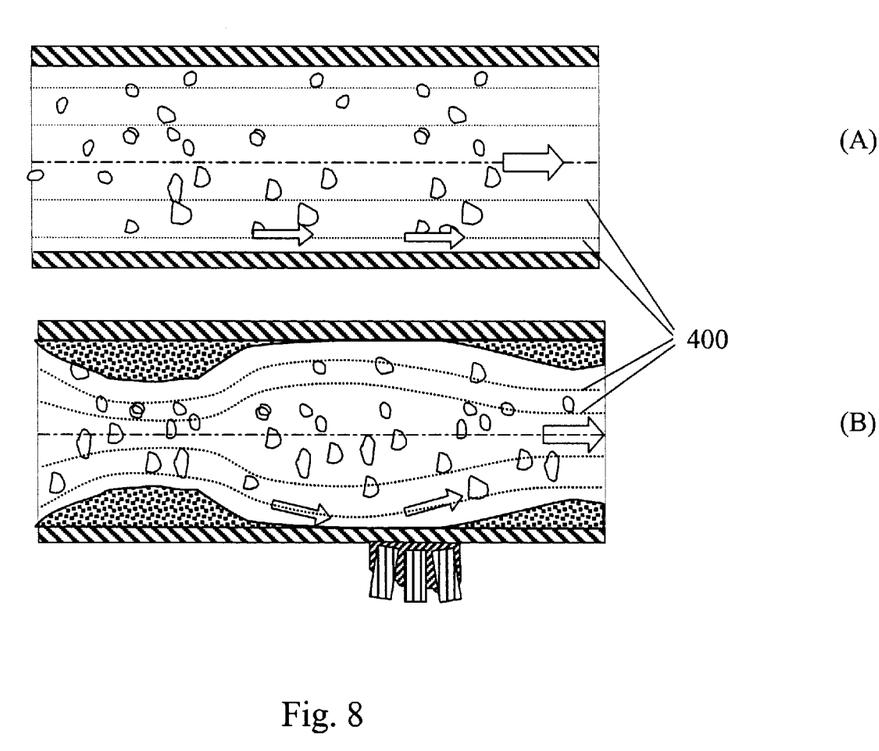
FIG. 8 is a schematic illustration showing how the apparatus of FIG. 7 can be used.

Very often, the extent of deposit buildup is not uniform and varies in thickness along the length of the pipeline. This variation in thickness of the deposits will tend to cause localized variation in the direction of the fluid flow stream close to the wall. By measuring and monitoring the direction of the velocity, qualitative assessment of deposits upstream and downstream of the sensor can be made. As shown in FIGS. 7 and 8, with the use of at least two receivers in conjunction with a transmitter, the direction of the fluid flow can be determined from the Doppler frequencies obtained from each receiver.

Referring particularly to FIG. 7, a preferred embodiment for sensing direction uses two receivers 110, 120 in conjunction with a transmitter 115. Transmitter 115 insonifies the fluid in a direction that is nearly perpendicular to the direction of the average flow velocity. Receivers 110 and 120 are placed at inclinations $\theta_{Rx1}$ and $\theta_{Rx2}$, respectively, with respect to the axis of transmitter 115. The inclinations are preferably set so as to develop an overlapping insonification region 300 near the boundary of the fluid and the pipe wall or deposit layer. It is not necessary that the inclinations $\theta_{Rx1}$ and $\theta_{Rx2}$ be equal. It should be noted that the flow velocity near the wall will not remain perpendicular to the transmitter under certain conditions such as turbulence or constrictions in the upstream or downstream side of the pipe. Under such conditions, the direction of flow may be at angle $\theta_T$ with respect to transmitter 115.

The scattered ultrasonic signals that reflect from scatterers 118 near the wall are picked up by receiver 110 as $R_{x1}$ and by receiver 120 as $R_{x2}$. These signals contain a sum of the Doppler frequency shifts associated with projections of the velocity components along the transmitter and along the receivers. Thus, $R_{x1}$ measures velocity in the direction of the center line of receiver $R_{x1}$ as given by Equation (4).

$$V_{x1} = V/[\cos\theta_T + \cos(\theta_T + \theta_{Rx1})]. \quad (4)$$

Similarly, $R_{x2}$ measures velocity $V_{x1}$ in the direction of the center line of receiver $R_{x2}$ as given by Equation (5).

$$V_{x2} = v/[\cos\theta_T + \cos(\theta_T - \theta_{Rx2})] \quad (5)$$

The values of $\theta_{Rx1}$ and $\theta_{Rx2}$ are known. $V_{x1}$ and $V_{x2}$ are calculated based on the Doppler frequency shifts in receivers $R_{x1}$ and $R_{x2}$. Equations (4) and (5) can be simultaneously solved to calculate values of $\theta_T$ and V. $\theta_T$ varies from $-90°$ to $+90°$.

Referring now to FIG. 8, a transmitter/receiver group 110, 115, 120 such as that described above can be used to detect constrictions upstream and downstream of itself Flowlines 400 represent the travel path of the fluid. For the unconstricted flow shown in FIG. 8(A), the flowlines are uniformly spaced. When deposits constrict the flow path, as shown in FIG. 8(B), the flowlines tend converge as the flow moves toward a constriction or diverge as the flow moves away from a constriction. Thus, knowing the direction of the velocity vector at a given point along the length of the pipe allows the system to detect deposit buildup upstream and downstream of the sensor location.

Applications include detection of and quantification of deposition on a flowline, measurement of flow velocity, determination of flow blockage ahead or behind the sensor group, measurement of individual phase velocities and slip velocities, and monitoring flow direction of individual phases.

The disclosed Doppler method, when used with one sensor set, provides localized, point deposit measurement. Likewise, the present system, when mounted at multiple positions along the pipeline, may provide distributed deposition profile measurement over the flowline of long distance. Both the localized and distributed deposit measurements, along with temperature and pressure measurements, can provide information about fluid flow, and provide data that assist in evaluating deposit behavior. In turn, this information can be used to help operators deploy appropriate means for deposit removal and prevention.

While a preferred embodiment of the invention has been described, it will be understood that variations can be made to the apparatus described herein without departing from the scope of the claimed invention.

What is claimed is:

1. A method for monitoring and measuring the buildup of deposits on the inner surface of a pipeline containing flowing fluid, comprising:
   (a) transmitting a first acoustic signal into the pipeline through the pipeline wall;
   (b) receiving echoes of the transmitted signal; and
   (c) determining from the received echoes how far from the pipeline inner surface the interface between the deposits and the flowing fluid lies.

2. The method according to claim 1 wherein step (c) includes using the Doppler frequency shift of echoes from the flowing fluid to locate the deposit-fluid interface.

3. The method according to claim 1, further including the step of gating the echoes.

4. The method according to claim 1 wherein step (c) includes measuring the Doppler frequency shift of the echoes from at least two points in the flowing fluid and extrapolating the location of the zero velocity.

5. The method according to claim 1 wherein the first transmitted signal is not normal to the pipeline axis.

6. The method according to claim 1, further including the step of using the reflected echo from the pipe inner surface to determine the thickness of the deposits.

7. The method according to claim 1, further including the steps of transmitting a second signal into the pipeline and determining the direction of fluid flow inside the pipe using received echoes of the first and second signals.

8. An apparatus for monitoring and measuring the buildup of deposits on the inner surface of a pipeline containing flowing fluid, comprising:
   a first transmitter in acoustic communication with the pipeline wall and generating a transmitted signal;
   a first receiver in acoustic communication with the pipeline wall and generating received echo signal from a received signal comprising the reflection of the transmitted signal off the flowing fluid; and
   a microprocessor for determining from the received echo signal how far from the pipeline inner surface the interface between the deposits and the flowing fluid lies.

9. The apparatus according to claim 8 wherein the microprocessor uses the Doppler frequency shift of echoes from the flowing fluid to locate the deposit-fluid interface.

10. The apparatus according to claim 9 wherein the microprocessor time-gates the echoes.

11. The apparatus according to claim 8 wherein the microprocessor measures the Doppler frequency shift of the echoes from at least two points in the flowing fluid and extrapolates the location of the zero velocity.

12. The apparatus according to claim 8 wherein the transmitted signal is not normal to the pipeline axis.

13. The apparatus according to claim 12 wherein the received signal is not normal to the pipeline axis.

14. The apparatus according to claim 8 wherein the microprocessor uses the reflected echo from the pipe inner surface to determine the thickness of the deposits.

15. The apparatus according to claim 8, further including a second transmitter for transmitting a signal into the pipeline, wherein the microprocessor determines the direction of fluid flow inside the pipe using received echoes of the first and second signals.

16. A method for monitoring and measuring the buildup of deposits on the inner surface of a pipeline containing flowing fluid, comprising:

(a) tansmitting a first acoustic signal into the pipeline through the pipeline wall;

(b) receiving echoes of the signal; and (c) using the Doppler frequency shift of the received echoes to determine how far from the pipeline inner surface the interface between the deposits and the flowing fluid lies.

17. The method according to claim 16, further including the step of time-gating the echoes.

18. The method according to claim 17 wherein step (c) includes measuring the Doppler frequency shift of the echoes from at least two points in the flowing fluid and extrapolating the location of the zero velocity.

19. The method according to claim 16 wherein the first transmitted signal is not normal to the pipeline axis.

20. The method according to claim 16, further including the step of using the reflected echo from the pipe inner surface to determine the thickness of the deposits.

21. The method according to claim 16, further including the steps of transmitting a second signal into the pipeline and determining the direction of fluid flow inside the pipe using received echoes of the first and second signals.

* * * * *